United States Patent
Grohol et al.

(10) Patent No.: US 11,612,881 B2
(45) Date of Patent: Mar. 28, 2023

(54) PROCESS FOR PREPARING AN EPOXIDATION CATALYST

(71) Applicant: Dow Technology Investments LLC, Midland, MI (US)

(72) Inventors: Daniel Grohol, Midland, MI (US); Thomas Z. Srnak, Arlington Heights, IL (US); Cathy L. Tway, Midland, MI (US); George L. Athens, Midland, MI (US); Kyle R. Essenmacher, Midland, MI (US); Gary M. Seabolt, Freeport, TX (US); Tim D. Munro, Midland, MI (US)

(73) Assignee: Dow Technology Investments LLC, Midland, MI (US)

( * ) Notice: Subject to any disclaimer, the term of this patent is extended or adjusted under 35 U.S.C. 154(b) by 181 days.

(21) Appl. No.: 16/771,372

(22) PCT Filed: Nov. 30, 2018

(86) PCT No.: PCT/US2018/063193
§ 371 (c)(1),
(2) Date: Jun. 10, 2020

(87) PCT Pub. No.: WO2019/133174
PCT Pub. Date: Jul. 4, 2019

(65) Prior Publication Data
US 2021/0178367 A1    Jun. 17, 2021

Related U.S. Application Data

(60) Provisional application No. 62/611,177, filed on Dec. 28, 2017.

(51) Int. Cl.
*B01J 23/50* (2006.01)
*C07D 301/10* (2006.01)
*B01J 21/04* (2006.01)
*B01J 35/10* (2006.01)
(Continued)

(52) U.S. Cl.
CPC .............. *B01J 23/50* (2013.01); *B01J 21/04* (2013.01); *B01J 35/1061* (2013.01);
(Continued)

(58) Field of Classification Search
CPC ........ B01J 23/50; B01J 21/04; B01J 35/1061; B01J 35/1066; B01J 35/1071;
(Continued)

(56) References Cited

U.S. PATENT DOCUMENTS 3,563,913 A    2/1971   de Krijger et al.
4,242,235 A    12/1980  Cognion et al.
(Continued)

OTHER PUBLICATIONS

Wikipedia, Surfactant, May 2016, p. 1-10. (Year: 2016).*
(Continued)

*Primary Examiner* — Taylor V Oh

(57) ABSTRACT

A process for preparing a silver-containing catalyst for the oxidation of ethylene to ethylene oxide (EO) including the steps of: providing a support having pores; providing a silver-containing impregnation solution; adding an amount of surfactant to the impregnation solution; contacting the support with the surfactant-containing impregnation solution; and removing at least a portion of the impregnation solution prior to fixing the silver upon the carrier in a manner which preferentially removes impregnation solution not contained in the pores. The use of the surfactant results in improved drainage of the silver impregnation solution from the carrier exteriors during the catalyst synthesis. As a result, the amount of silver-containing impregnation solution necessary for the synthesis of the EO catalyst was reduced by up to 15% without reducing the catalyst performance.

13 Claims, 3 Drawing Sheets

(51) Int. Cl.
  *B01J 37/02* (2006.01)
  *B01J 37/08* (2006.01)
(52) U.S. Cl.
  CPC ....... *B01J 35/1066* (2013.01); *B01J 35/1071* (2013.01); *B01J 35/1076* (2013.01); *B01J 35/1095* (2013.01); *B01J 37/0203* (2013.01); *B01J 37/0236* (2013.01); *B01J 37/086* (2013.01); *C07D 301/10* (2013.01)
(58) Field of Classification Search
  CPC ................ B01J 35/1076; B01J 35/1095; B01J 37/0203; B01J 37/0236; B01J 37/086; B01J 35/0073; B01J 37/009; B01J 37/0207; C07D 301/10
  USPC .................................. 502/348; 549/523, 533
  See application file for complete search history.

(56) References Cited

U.S. PATENT DOCUMENTS

| | | |
|---|---|---|
| 5,187,140 A | 2/1993 | Thorsteinson et al. |
| 5,734,068 A | 3/1998 | Klopries et al. |

OTHER PUBLICATIONS

PCT/US2018/063193 The International Search Report and The Written Opinion of the International Searching Authority, dated Mar. 7, 2019.
PCT/US2018/063193 International Preliminary Report on Patentability, dated Mar. 13, 2020.

\* cited by examiner

PROCESS FOR PREPARING AN EPOXIDATION CATALYST

FIELD

The present invention is related to a process for preparing an epoxidation catalyst. More specifically, the present invention is related to a process for preparing a silver-containing catalyst useful for olefin epoxidation reactions.

BACKGROUND AND SUMMARY OF THE INVENTION

The production of ethylene oxide via a catalytic epoxidation of ethylene in the presence of oxygen and in the presence of a silver-based catalyst is known. In general, the epoxidation reaction includes the step of contacting a feed containing at least ethylene and oxygen with a supported silver-containing catalyst resulting in the production of the corresponding ethylene oxide (EO). Commercial catalysts used for producing EO are known to include silver particles supported on an alumina support. Such catalysts are typically prepared by impregnating carrier support made from porous alumina with silver-containing impregnation solution, followed by heat treating (sometimes referred to as "roasting") the impregnated support. A high surface tension undesirably causes excess silver impregnation solution to cling on the external surfaces of the formed carrier pellet material.

Excess silver impregnation solution present on the support's external surfaces causes several undesirable consequences related both to the cost associated with the catalyst preparation and to catalyst performance. During catalyst production, a portion of the excess solution can be lost in catalyst processing equipment downstream of impregnation equipment, resulting in silver losses, equipment fouling, and decreased catalyst production plant reliability and run time. When a catalyst is made utilizing a calcination step where the catalyst pellets are heat treated by passing a gaseous stream through a catalyst bed or layer, the presence of excess impregnation solution on the catalyst carrier pellet exterior surfaces can be particularly problematic. If the catalyst calcination step is done utilizing a mesh belt, the excess solution can transfer to the belt, resulting in blockage of the openings with silver deposits. Such blockages can result in reduced gas flow, potentially affecting the quality of the calcination process and subsequent final catalyst quality. As a result, such fouling requires stoppage of the synthesis process and cleaning. The impregnation solution clinging to the surface of the porous alumina carrier that is not removed during the calcination process can agglomerate into relatively large silver particles on the alumina surface. These silver agglomerates have low surface areas, causing them to be catalytically inactive, and therefore ineffective as catalysts for EO or other production.

It would therefore be desirable to reduce the excess of silver-containing solution which clings to the carrier during the impregnation process.

It has been discovered that the addition of various surfactants into the silver impregnation solution can improve its drainage from the carrier exteriors during the catalyst synthesis. As a result, the amount of silver-containing solution consumed for the synthesis of the EO catalyst was reduced by up to 15% without reducing the catalyst performance. While the improvement is most apparent in more complex carrier shapes such as pentarings, the addition of surfactants to the impregnation solution also produces benefits in more typical shapes like standard monoring carriers.

Additionally, the use of surfactants can deliver EO catalysts with reduced external surface agglomeration of silver, catalyst handling post calcination can be simplified due to reduced dust and debris formation. Since the generation of dust during catalyst loading and during the catalysis process is known to increase pressure drop, the use of surfactants may further improve silver utilization in the EO catalysis process, and it could also result in improved plant performance due to more consistent pressure drop across the reactor tube sheet and shorter plant turnaround times.

One embodiment of the present invention is directed to a process for preparing a silver-containing catalyst for the oxidation of ethylene to ethylene oxide (EO) including the steps of:

(a) providing a support having pores;
(b) providing a silver-containing impregnation solution;
(c) adding an amount of surfactant to the impregnation solution;
(d) contacting the support with the surfactant-containing impregnation solution;
(e) removing at least a portion of the silver impregnation solution prior to subsequent catalyst preparation steps in a manner which preferentially removes impregnation solution not contained in the pores.

In another embodiment, the process for preparing a silver-containing catalyst may include the additional step of:

(f) roasting (e.g., calcining), at least once, the impregnated catalyst support member from step (e) for a time and temperature sufficient to form a silver-containing catalyst useful for the epoxidation of olefins.

In another embodiment, the selective removal of the excess of silver solution means in step (e) may include simply allowing the impregnated catalyst support member to drain using gravity.

In still another embodiment, the selective removal means in step (e) may include a centrifuge for centrifuging the impregnated catalyst support member to remove at least a portion of impregnated solution not contained in the support pores.

In an optional embodiment, the impregnation step (d) and/or the removing step (e) may be repeated, at least one more time, for a time sufficient to remove further the silver impregnation solution contained in the catalyst support member.

In further embodiment, the removing step (e) may be carried out at least two times before the roasting step (f). The removing step (e) is advantageously performed at a centrifugal force and for a period of time sufficient to remove the silver solution from the external surface and to provide the support with a more evenly distributed silver particle size in the pores of the catalyst support after roasting.

In yet other embodiments, any one or more of the above steps (a)-(f) can optionally be repeated any number of times as desired and sufficiently to control the amount of silver deposited in the pores of the catalyst support.

In still another embodiment, the support has a first set of support pores having a first size range and at least a second set of support pores having a second size range wherein the second size range is smaller than the first size range, and wherein the removing step (e) preferentially removes silver impregnation solution contained in the first set of support pores of the porous multimodal catalyst support as compared to silver impregnation solution contained in the at least second set of pores of the porous multimodal catalyst support.

Also provided in the present application is a reaction system for producing ethylene oxide from a feed comprising ethylene and oxygen over an ethylene oxide catalyst prepared by the process of the present invention.

BRIEF DESCRIPTION OF THE DRAWINGS

The drawings show non-limiting embodiments of the present invention wherein.

DETAILED DESCRIPTION

Figure 1:
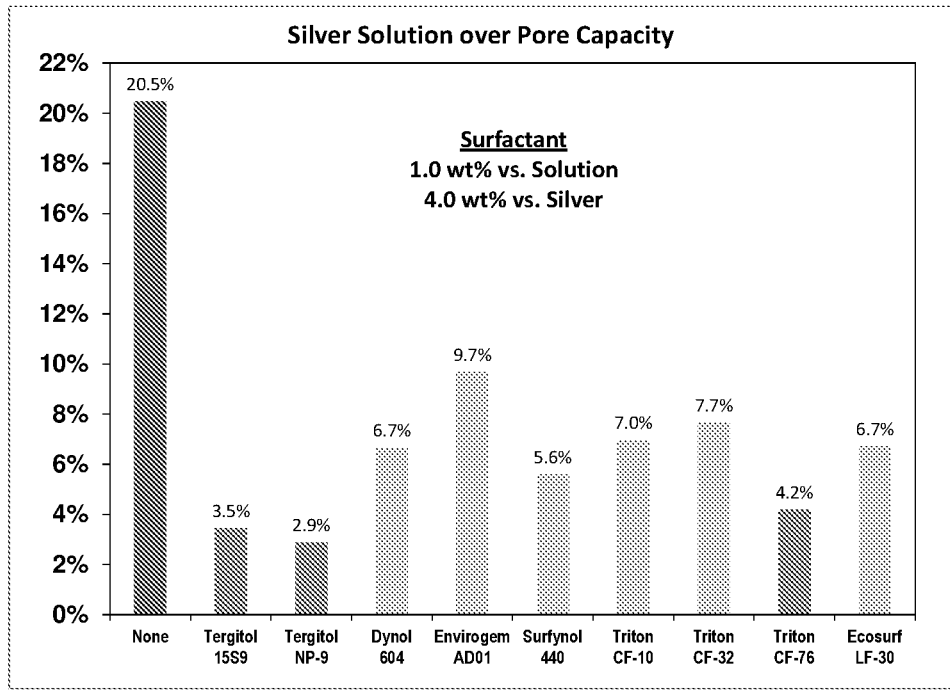
FIG. 1 is a graphical representation showing the effectiveness of various surfactants added at 1% by weight, in allowing excess silver impregnation solution to drain from the support.

"Catalyst" herein means a substance that increases the rate of a chemical reaction.

In an epoxidation reaction, ethylene reacts with oxygen or an oxygen-containing gas in the presence of a supported silver-containing catalyst in a reactor to form ethylene oxide. The epoxidation reaction can be characterized in terms of "activity", "selectivity" and/or "productivity" of the epoxidation reaction.

For example, the "selectivity" of an epoxidation reaction, which is synonymous with "efficiency," refers to the relative amount (as a fraction or in percent) of converted or reacted ethylene that forms the corresponding ethylene oxide product. The terms "efficiency" and "selectivity" are used interchangeably herein. For example, the "efficiency to ethylene oxide" refers to the percentage on a molar basis of converted or reacted ethylene that forms ethylene oxide. The "yield" of ethylene oxide refers to the net number of moles of ethylene oxide produced by the process divided by the net number of moles of ethylene fed to the process for any given time period.

The "activity" of a catalyst, for example in a fixed bed reactor, is generally defined as the reaction rate towards the desired product per unit of catalyst volume in the reactor. The activity relates to both the total number of available active sites on the catalyst and the reaction rate of each site.

In addition, the "activity" of an epoxidation reaction can be quantified in a number of ways, one being the mole percent of ethylene oxide contained in an outlet stream of a reactor relative to that in an inlet stream of the reactor (the mole percent of olefin oxide in the inlet stream typically, but not necessarily, approaches zero percent) while the reactor temperature is maintained substantially constant; and another being the temperature required to maintain a given rate of ethylene oxide production. In some instances, activity is measured over a period of time in terms of the mole percent of ethylene oxide produced at a specified constant temperature. Alternatively, the "activity" of an epoxidation reaction can be measured as a function of the temperature required to sustain production of ethylene oxide at a specified rate, given other conditions such as pressure and total moles in the feed.

"Promoters," sometimes referred to as "inhibitors" or "moderators," refer to materials that enhance the performance of the catalysts by either increasing the rate towards the desired formation of ethylene oxide and/or suppressing the undesirable oxidation of ethylene or ethylene oxide to carbon dioxide and water, relative to the desired formation of ethylene oxide.

The terms "reaction temperature," "epoxidation temperature" or "epoxidation reaction temperature" refer to any selected temperature(s) that are directly or indirectly indicative of the catalyst bed temperature of a reactor. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor inlet or outlet coolant temperature.

As used herein, the term "reaction product" includes both unreacted feed components and those components that are generated as a result of a chemical reaction. In an ethylene oxide production process, for example, the "reaction product" includes ethylene oxide product; and if present, any by-products (such as carbon dioxide) and/or unreacted feed components (such as ethylene, oxygen, and/or chlorides).

"Silver loading" herein means weight percent or weight fraction of the catalyst that is silver and based on the calcined catalyst. Silver loading can be determined by X-ray fluorescence, titration or other means known to those skilled in the art (Neutron activation analysis, NAA).

"Silver particle size" herein refers to average particle size in nanometers as measured by dynamic pulse CO chemisorption method, scanning electron microscopy (SEM) or other means known to those skilled in the art.

Dynamic pulse CO chemisorption method enables the determination of exposed silver sites and is based on the reaction of CO on an oxidized silver surface, producing $CO_2$. The average particle size diameter from the CO titration experiments can be determined by the following expression:

$$d = \frac{\sigma_{Ag}}{N_A} \frac{6}{\rho_{Ag}} \frac{n_{Ag}}{n_{CO_2}}$$

wherein $\sigma_{Ag}$ is the average atomic surface density of silver atoms, $\rho_{Ag}$ is the density of silver, NA is the Avogadro's number, $n_{Ag}$ is the number of moles of silver atoms present on the sample and $n_{CO2}$ is the total number of moles of $CO_2$ produced. The stoichiometry between the surface atoms and adsorbed gas is considered to be equal to 1.

A "multimodal pore size distribution", with reference to a catalyst support, herein means a support wherein the pore size is a continuous probability distribution with at least two different modes determined by methods (such as mercury porosimetry) known by those skilled in the art.

A "bimodal pore size distribution", with reference to a catalyst support, herein means a continuous probability distribution of pore size of pores with two different modes.

The terms "control" or "controlling", with reference to a particle size, herein means primarily using silver concentration in the impregnation solution in conjunction with impregnation, calcination, and a selective removal means to provide silver particles of a desired particle size.

One embodiment of the present invention is directed to a process for preparing a silver-containing catalyst for the oxidation of ethylene to ethylene oxide (EO) including the steps of:
(a) providing a support having pores;
(b) providing a silver-containing impregnation solution;
(c) adding an amount of surfactant to the impregnation solution;
(d) contacting the support with the surfactant-containing impregnation solution;
(e) removing at least a portion of the impregnation solution prior to fixing the silver upon the carrier in a manner which preferentially removes impregnation solution not contained in the pores.

For each embodiment, it should be understood that the surfactant may be added at any stage of the preparation of the impregnation solution, including the preferred embodiment of adding the surfactant after the impregnation solution has otherwise been completed.

The resulting silver-based catalyst of the present invention is useful for the epoxidation of ethylene to form ethylene oxide, among other potential uses.

The broad general procedure of the present invention for preparing the silver-based catalyst includes at least the following steps: preparing an impregnation solution comprising silver-containing component(s) useful for impregnating a porous support member, contacting and impregnating the support member with the prepared impregnation solution, and then removing at least a portion of the impregnated impregnation solution from the support, in a manner which preferentially removes solution which has not entered the pores of the support.

In one preferred embodiment, the process of the present invention can include for example a five-step process, including the steps of:
(a) providing a support having pores;
(b) providing a silver-containing impregnation solution;
(c) adding an amount of surfactant to the impregnation solution;
(d) contacting the support with the surfactant-containing impregnation solution;
(e) removing at least a portion of the impregnation solution prior to fixing the silver upon the carrier in a manner which preferentially removes impregnation solution not contained in the pores; and
(f) roasting (e.g., calcining) the porous catalyst support member from step (e) to chemically reduce the silver-containing solution component to metallic silver and deposit it on the interior and exterior surfaces of the porous catalyst support member to form a catalyst.

In other embodiments, the process of the present invention may include one impregnation step or a sequence of two or more impregnation steps. The impregnated support from the impregnation step can then be treated by or subjected to a removal means such as a centrifugation step, followed by a calcination step. Any of the impregnating, centrifuging, or roasting steps of the present invention process may be carried out once or if desired, and in some embodiments, any or all of the steps may be carried out two or more times.

In another embodiment the process of the present invention wherein the catalyst is subjected to a sequence of a first impregnation step, a first centrifugation step, and a first calcination step in series followed by a sequence of a second impregnation step, a second centrifugation step, and a second calcination step in series. Such steps can be repeated multiple times. As a result of the process the catalyst essentially undergoes the series of impregnation, centrifugation and calcination steps two or more times to produce a catalyst product.

In still another embodiment, the process of the present invention for preparing a silver-containing catalyst for the epoxidation of olefins can include the steps of:
(a) providing a porous multimodal support having at least two modes of pore size distributions;
(b) providing a surfactant-containing, silver-containing, impregnation solution for impregnating the pores of the porous multimodal support;
(c) impregnating the porous multimodal support with the impregnation solution from step (b) to provide the porous multimodal support with a first amount of impregnation solution;
(d) centrifuging the impregnated silver-containing solution from the porous multimodal support;
(e) roasting the impregnated porous multimodal support from step (d);
(f) impregnating the porous multimodal support with the impregnation solution from step (b) or with a different impregnation solution to provide the porous multimodal support with a second amount of impregnation solution;
(g) centrifuging the silver-containing impregnation solution from the porous multimodal support from step (f) to provide the porous multimodal support with a third amount of impregnation solution remaining in the support pores; and
(h) roasting the impregnated porous multimodal support from step (g) for a time and temperature sufficient to form a silver-containing catalyst useful for epoxidation of olefins; and wherein the centrifugation steps (d) and (g) are carried out under different centrifugation conditions.

In yet another embodiment, the impregnated centrifuged catalyst can be subjected to two sequential calcination steps, i.e., a first calcination step followed sequentially by a second calcination step at the same or different temperature to provide a catalyst product. Likewise, the calcination steps in steps (e) and (h) above can utilize different temperatures, gas flows, and/or gas compositions.

In any of the above embodiments, the extent of solution removal may remove at least 40 percent (%), at least 50%, at least 70% or at least 90% of the impregnated surfactant-and-silver-containing solution present on the exterior surfaces of the support. Further in embodiments with multimodal pores, the extent of solution removal from the surface and the first (i.e., larger) set of pores may be at least 20%, 30%, 50% or 80%. In still another embodiment, up to 100% of the surfactant-and-silver-containing impregnation solution present on the exterior surface and in the at least first set of support pores of the porous multimodal support can be removed.

The process for preparing a catalyst in accordance with the present invention starts with a first step of providing a porous support (also known as a "support") that is to be impregnated with an impregnation solution. The catalyst preparation process described herein can be applied to different types of supports, including those having a multimodal pore size distribution such as a bimodal support and to other catalysts prepared via impregnation techniques. A multimodal support includes a support having at least two different pore modes. In general, the porous multimodal support of the present invention may have at least a first set of support pores of a first size range and at least a second set of support pores of a second size range wherein the second size range of the second set of support pores is smaller than the first size range of the first set of support pores. In general, the pore sizes in the support will range from 0.01 µm to 100 µm.

For porous supports having pores with at least two distinct ranges of pore sizes, the first set (i.e. the set with the larger pore size) of pore sizes may advantageously be in the range of from about 3 µm to about 100 µm in one embodiment and from about 5 µm to about 50 µm in another embodiment, and the second set of support pores may be in the range of from about 0.01 µm to about 3 µm in one embodiment and from about 0.01 µm to about 1 µm in another embodiment.

The supports may comprise any of the known porous refractory structures or support materials, so long as whatever the porous refractory material chosen is relatively inert or behave in a beneficial manner in the presence of the chemicals and processing conditions employed in the application in which the supports will be utilized.

The support may be selected from a wide range of support materials including for example, natural or artificial inorganic support materials such as silicon carbide, clays, pumice, zeolites, charcoal and alkaline earth metal carbonates, such as calcium carbonate and mixtures thereof. Other embodiments may include refractory support materials, such as alumina, magnesia, zirconia and silica; and mixtures thereof. In one preferred embodiment, the support material can be alpha-alumina. In one exemplary embodiment, silver is deposited on the alpha alumina catalyst support and optionally one or more promoters can be deposited on the catalyst as well.

The materials used for the support may be used with or without a binder. The binder, when used, can be for example an inorganic type of material.

Generally, the porous support is prepared by well-known methods. For example, several well-known methods of preparing supports suitable for use in alkene oxide catalysts are described in WO 2013/148417 A1; and U.S. Pat. Nos. 4,379,134; 4,806,518; 5,063,195; 5,384,302; and 6,831,037 incorporated herein by reference.

For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity and/or pore size distribution after its removal during the calcination step. The levels of impurities in the finished support are determined by the purity of the raw materials used, and their degree of volatilization during the calcination step. Common impurities may include silica, alkali and alkaline earth metal oxides and trace amounts of metal and/or non-metal-containing additives.

The alumina can be of a very high purity grade, that is, at least 98 percent by weight or weight percent (wt %) alpha-alumina, any remaining components being silica, alkali metal oxides (for example, sodium oxide) and trace amounts of other metal-containing and/or non-metal-containing additives or impurities. Likewise, the alumina can be of a lower purity, that is, 80 wt % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the support may comprise promoters for the intended reaction, for example, rhenium, (such as rhenates) and molybdenum.

The alpha-alumina support may have a pore volume of at least 0.3 cubic centimeters per gram ($cm^3/g$) in one embodiment, and from about 0.4 $cm^3/g$ to about 2.0 $cm^3/g$ in another embodiment; pore diameters may range from about 0.1 micron to about 50 microns.

The alpha-alumina support may have a specific surface area of at least about 0.5 square meters per gram ($m^2/g$) in one embodiment, and at least about 0.7 $m^2/g$ in another embodiment. The surface area of the alpha-alumina support may be less than about 10 $m^2/g$ in one embodiment, and less than about 5 $m^2/g$ in another embodiment.

The alpha-alumina support useful in the present invention can be of any suitable shape. Exemplary shapes of the support includes pills, chunks, tablets, pieces, pellets, rings, spheres, wagon wheels, toroids having star shaped inner and/or outer surfaces, and the like.

The support can be of any size suitable for employment in reactors. For example, in a fixed bed ethylene oxide reactor having a plurality of parallel elongated tubes (in a suitable shell) 1 inch to 3 inches (2.5 cm to 7.5 cm) outer diameter and 15 feet to 45 feet (4.5 m to 13.5 m) long filled with catalyst, it is desirable to employ alpha alumina support having a rounded shape, such as, for example, spheres, pellets, rings, cross-partitioned rings, penta-rings, tablets, and the like, having diameters from 0.1 inch (0.25 cm) to 0.8 inch (2 cm).

The impregnation solution useful in the present invention can be any suspension of nanoparticles in a liquid medium as such suspensions would benefit from the reduction or elimination of liquid clinging to the exterior surfaces of the support. The preferred impregnation solution includes silver-containing impregnation solutions. While in one embodiment, a bimetallic system can be used which may include silver and another metal such as copper or gold, typically silver alone is impregnated into a support. The silver impregnation solution used to impregnate the support comprises a silver component in an impregnating medium such as solvent or complexing/solubilizing agent as disclosed in U.S. Pat. No. 5,187,140 incorporated herein by reference.

The particular silver component employed in the present invention may be chosen, for example, from among silver complexes, nitrate, silver oxide or silver carboxylates, such as silver acetate, oxalate, citrate, phthalate, lactate, propionate, butyrate and higher fatty acid salts; and mixtures thereof. In another embodiment, silver oxide complexed with amines may be the form of silver that may be used in the practice of the present invention.

A wide variety of solvents or complexing/solubilizing agents may be employed to solubilize nanoparticles including the preferred silver component described above to the desired concentration in the impregnating medium or solution. The solvent can be any conventional solvent or any complexing/solubilizing agent known in the art so long as the solvents or complexing/solubilizing agents can solubilize the silver component to the desired concentration in the impregnation solution, and the solvent or the complexing/solubilizing agent does not detrimentally affect the performance properties of the catalyst. Among the solvents or complexing/solubilizing agents suitable for this purpose may include for example lactic acid (as disclosed in U.S. Pat. Nos. 2,477,436 and 3,501,417); ammonia (as disclosed U.S. Pat. No. 2,463,228); alcohols, such as ethylene glycol (as disclosed in U.S. Pat. Nos. 2,825,701 and 3,563,914); and amines and aqueous mixtures of amines (as disclosed in U.S. Pat. Nos. 2,459,896; 3,563,914; 3,215,750; 3,702,259; 4,097,414; 4,374,260; and 4,321,206) all of which are incorporated herein by reference. A combination of two or more of the above solvents or complexing/solubilizing agents may also be used in the impregnation solution of the present invention.

The surfactant for use in the present invention can be any material capable of reducing the surface tension between the silver impregnation solution and the support surface, which does not unduly interfere with subsequent catalyst manufacturing processing steps or final catalyst performance. Examples of suitable well-known classes of surfactants for various applications include, but are not limited to nonylphenol ethoxylates, alkyl polyglucosides, phosphate esters, secondary alcohol alkoxylates, alkylphenyloxide disulfonate salts, low foam surfactants, sulfates and sulfonates. Commercially available compounds which may be useful in the present invention include: TERGITOL™ 15S9, TERGITOL™ NP-9, TRITON™ CF-10, TRITON™ CF-32, TRITON™ CF-76 and ECOSURF™ LF 30 (all from the Dow Chemical Company); DYNOL™ 604, and Surfynol® 440 (both from Evonik Industries); and ENVIROGEM® ADO1 (from Air Products).

It is also contemplated that two or more surfactants may be used together.

The surfactant should be added in amount to reduce the amount of solution remaining on the exterior surfaces of the support and/or at least the first set of pores with the larger pore size. In general it is suggested that the surfactant should be added in an amount of from 0.05% by weight of the solution, preferably 0.1% by weight up to 2% by weight, more preferably 1% by weight. The desired amount of surfactant may depend on the concentration of silver (or other nanoparticles) in the solution. For silver-containing solutions, it is suggested that the surfactant be added in an amount of 0.1 wt % to 8 wt % preferably about 2 wt % to 6 wt % of surfactant per unit silver used (for example, if the solution contains 26 wt % silver, then a suggested amount of surfactant to be added to the solution may be about 4% by weight). It is believed that amounts of surfactants lower than these suggested amounts will still improve the removal of undesired impregnation solution relative to using no surfactant, but the improvement will be less. An amount of surfactant larger than these suggested amounts is also expected to improve the removal of undesired impregnation solution, but with increasing amount of surfactant, its relative effectiveness is expected to decrease. It is also expected that the ranges of most effective surfactant percentage will differ for different surfactants, combinations of surfactants used, or impregnation solution compositions. Generally, the support is impregnated with an impregnation solution that contains silver, in the amount capable of catalyzing the direct oxidation of the alkene with oxygen or an oxygen-containing gas to the corresponding alkene oxide. In making such a catalyst, the support may be typically impregnated (one or more times) to allow the desired amount of silver to be deposited on the support.

Generally, the amount of silver component that is dissolved in the silver impregnation solution is more than that ultimately provided on the finished catalysts per impregnation. For example, $Ag_2O$ can be dissolved in a solution of oxalic acid and ethylenediamine to an extent of approximately [~] 30 wt %. Vacuum impregnation of such a solution onto an alpha alumina support of ~0.7 cc/g porosity results in a catalyst containing ~25 wt % of silver based on the entire weight of the catalyst. Accordingly, in order to obtain catalysts having a silver loading greater than about 25 wt %, greater than about 30 wt %, or more, it is necessary to subject the support to at least two or more sequential impregnations with silver solution, with or without promoters, until the desired amount of silver is deposited on the support. Two or more impregnations may be used to make the catalysts of the present invention to achieve the desired loading of silver in the resultant catalyst.

As it is known, the number of impregnations, the concentration of solution used for each impregnation and the calcination conditions are factors that can be used to fine tune the particle size of silver in the resultant catalyst. For example, the concentration of the silver salt can be higher in the latter impregnation solutions than in the first. In other instances, approximately equal concentrations of silver can be used during each impregnation step. In further instances, a greater concentration of silver can be used in the initial impregnation than in subsequent impregnations. Each of the impregnations may be followed by roasting or other procedure to render the silver insoluble.

In addition to the surfactant, various optional compounds or additives can be added to the impregnation solution including for example one or more promoters, alkali metals, alkali earth metals, and oxyanions, and mixtures thereof. In one embodiment, promoters can be materials that are introduced to catalysts during the preparation of the catalysts (e.g., solid phase promoters, also referred to as "catalyst promoters" herein). In another alternative embodiment, promoters can be gases that are introduced to the epoxidation reactor feed (gas phase promoters). In one example, an organic halide gas phase promoter may be added continuously to an epoxidation reactor feed to increase the catalyst efficiency and/or selectivity. For silver-based ethylene epoxidation catalysts, both solid and gas phase promoters are typically used during the catalytic process.

Suitable alkali metal promoter components can be used in forming the impregnation solution if desired. For example, the alkali metal promoter components may include all those promoters that are soluble in the particular solvent or solubilizing agent employed and that are compatible with the other components in the impregnation solution. Accordingly, inorganic and organic components of alkali metals, such as, nitrates, halides, hydroxides, sulfates and carboxylates may be used. As an illustration, alkaline earth salts such as salts of barium, calcium and magnesium can readily be solubilized in the impregnation solution and deposited upon the support in accordance with the process of the present invention.

The sequence of impregnating or depositing the surfaces of the support with silver and promoters is optional. Thus, impregnation and deposition of silver and salts may be effected coincidentally or sequentially, i.e., the promoters may be deposited prior to, during, or subsequent to silver addition to the support. The promoters may be deposited together or sequentially. For example, one or more of the salts may be deposited first, followed by the coincidental or sequential deposition of silver and additional or other salts.

Impregnation of the catalyst support may be effected using one or more solutions containing silver and promoters in accordance with well-known procedures for coincidental or sequential depositions. For coincidental deposition, following impregnation, the impregnated support is treated (e.g., by application of heat or a chemical treatment) in order to chemically reduce the silver component to silver metal and deposit the salts onto the catalyst surfaces.

For sequential deposition, the support is initially impregnated with silver or promoter (depending upon the sequence employed) and then treated as described above. This is followed by a second impregnation step and a corresponding heat or chemical treatment to produce the finished catalyst containing silver and promoters.

In one embodiment of the present invention, one or more promoters are added coincidentally with the silver. In another embodiment, one or more promoters are added to the catalyst in the very last silver impregnation step.

All the components of the impregnation solution are typically mixed and dispersed in a vessel at a temperature enabling the preparation of an effective impregnation solution. For example, the temperature during the mixing of the above components may be generally from about ambient temperature (23° C.) to about 70° C. in one embodiment, and from about ambient temperature to about 50° C. in another embodiment. The surfactant selected may be optimized for the desired impregnation temperatures.

The preparation of the impregnation solution of the present invention, and/or any of the steps thereof, may be a batch or a continuous process. The process and type of equipment used to prepare the impregnation solution may be any conventional process or equipment known in the art. For example, a mixing vessel is used to blend or mix the above components: the silver component, the solvent and optionally any other desirable additives such as promoter(s).

In general, a procedure for depositing silver catalytic material and any other additives such as promoters includes: impregnating a porous alumina support according to the present invention with a solution comprising a solvent or solubilizing agent, silver complex and one or more promoters, if desired. Impregnation of the support is generally the preferred technique for silver deposition, because it utilizes silver more efficiently than dry coating procedures, the latter being generally unable to effect substantial silver deposition onto the interior surfaces of the support. In addition, dry-coated catalysts are more susceptible to silver loss by mechanical abrasion.

The process and type of equipment used to entrain the silver-containing solution into the support may be any conventional impregnation process or equipment known in the art. For example, a vessel is used to contain the support, which is to be saturated with the impregnation solution described above, and the impregnation solution is passed through the support in the vessel. A particularly useful technique to ensure complete filling of the carrier pores employs applying a vacuum to evacuate the carrier pores prior to exposing the carrier to the impregnation solution.

"Surface area," as used herein, refers to the surface area of the supports as determined by the BET (Brunauer, Emmett and Teller) method by nitrogen as described in the Journal of the American Chemical Society 60 (1938) pp. 309-316 incorporated herein by reference. "Total pore volume" means pore volume of the support and is typically determined by mercury porosimetry. The measurements reported herein used the method described in Webb & Orr, Analytical Methods in Fine Particle Technology (1997), p. 155, incorporated herein by reference, using mercury intrusion to 60,000 psia using Micromeritics Autopore IV 9520, incorporated herein by reference, assuming 130° contact angle, 0.485 N/M surface tension of mercury. "Porosity" is the proportion of the non-solid volume to the total volume of material. Total pore volume as measured by mercury porosimetry or water absorption may be used to estimate open porosity by those of skill in the art. Although not of catalytic importance, closed pores will not be determined using these techniques. Put another way, porosity is defined as the accessible void volume (unoccupied space) divided by the total volume of the sample."

After the porous catalyst support is filled with the impregnation solution (also referred to herein as the "impregnated support"), any impregnation solution that is not absorbed into the pores of the support is referred to herein as "non-impregnated solution". This may include solution around and on the exterior surfaces of the support. The solution that has been impregnated or absorbed into the pores of a catalyst support is referred to herein as the "impregnated solution". It is a feature of this invention that the majority of the non-impregnated solution, if present, and at least a portion of the impregnated solution are removed from the impregnated support in distinct steps.

For example, following each impregnation of the catalyst support with silver-containing impregnation solution, it is desirable that remaining, extra, or excess non-impregnated solution be separated from the overall impregnated support by employing a conventional separation means such as filtering, draining or centrifuging. For example, the non-impregnated solution can be drained away from the impregnated support, i.e., the non-impregnated solution is physically separated from the external surface of the overall support. As another example, when centrifugation is used as the separation means, the centrifugation is used under operating conditions to separate non-impregnated solution from the external surface of the overall impregnated catalyst. Generally speaking, draining is most commonly used to separate any excess non-impregnated solution from the impregnated support.

For embodiments where the support has pores having two or more distinct ranges of pore sizes, then following any of the above described separation methods, the impregnated support can be subjected to a second removal method to selectively and physically remove at least a portion of the impregnated solution from support pores of the impregnated support having the larger pore size. Preferably, this second removal method comprises centrifugation.

When centrifugation is used as the removal means in the present invention, the centrifugation conditions may be chosen to selectively remove impregnated solution not only from the surface of the overall catalyst, but also from certain pores (that is the pores with the larger pore size) of the catalyst support. The centrifugation step separates the excess non-impregnated impregnation solution from the surface of the catalyst support that was not removed in a draining step (if used) and the impregnated solution from certain pores of the catalyst support. Generally, the important factors to consider for carrying out the centrifugation step of the present invention may include, for example, the speed of rotation (r.p.m.), radius of centrifuge, time, and temperature of centrifugation. The speed of rotation and the radius of the centrifuge determine the relative centrifugal force (RCF). RCF may be calculated using the following equation Eq. (1):

$$RCF = 1.12 R_c \cdot \left(\frac{r.p.m}{1000}\right)^2 \qquad \text{Eq. (1)}$$

wherein $R_c$ is the radius of the centrifuge (mm) and r.p.m. is the rotational speed in revolutions per minute.

The centrifugal force can be calculated from the following equation:

$$F_c = m\overline{\omega}^2 R_c = h\pi r^2 \rho \overline{\omega}^2 R_c \quad \text{Eq. (2)}$$

wherein m is the mass of liquid present within the pores, ω is the angular speed, r is the radius of the pore, h is the height of the liquid present in the pore, $R_c$ is the radius of the centrifuge, ρ is the density of the liquid. The height of the liquid inside the pore is determined by the balance between the surface tension force and the gravitational forces:

$$h = \frac{2\gamma\cos\theta}{r\rho g} \quad \text{Eq. (3)}$$

wherein θ is the contact angle.

To selectively remove the solution from pores having the larger pore size, the centrifugal force should be equal to the capillary force for the correspondent pore. The capillary force is calculated by the following equation:

$$F_{capillary} = h\gamma \cos\theta \quad \text{Eq. (4)}$$

As a summary the optimal RCF to remove the solution located inside a certain size of pores is determined by matching the capillary with the centrifugal force. Based on this the following relationship is obtained:

$$RCF = 0.1\left(\frac{\gamma\cos\theta}{\pi r^2 \rho}\right) \quad \text{Eq. (5)}$$

The physical properties expressed in Eq. (5) are temperature dependent and therefore may affect the efficiency of the centrifugation process.

To further illustrate the present invention employing equation (5) above, the following properties can be used in the equation: For the properties of impregnation liquid, $\gamma = 7.28 \times 10^{-2}$ N/m; θ=85°; and ρ=1493 kg m$^{-3}$ and assuming that the size of pore ranges from 1,000 μm to 1 μm, the centrifugal force (RCF) can be for example from about 0.1 to 1,500,000.

The centrifugation time can be for example from about 1 minute (min) to about 20 min in one embodiment, and from about 5 min to about 10 min in another embodiment. The temperature at which the centrifugation is performed can be a factor since it may determine the properties of the impregnation solution inside the pores and the way it interacts with the support. The centrifugation can be carried out at any suitable temperature; for example, not so high that the solution evaporates or decomposes in the centrifuge, or at a temperature not so low that the fluid is not flowable, i.e., the solution should remain sufficiently fluid and have the necessary rheology to be removable from the support by the centrifuge. In one general embodiment, for example, the centrifugation temperature can be from about 20° C. to about 80° C. In one embodiment for example, a silver amine oxalate solution of the type described herein in the Examples can be centrifuged at a temperature of from about 20° C. to about 40° C.

The centrifugation step of the present invention, and/or any of the steps thereof, may be a batch process; and the equipment used in the process may be any centrifuge and ancillary equipment well known to those skilled in the art.

The centrifugation step of the present invention process is important because centrifugation separates the excess non-impregnated impregnation solution from the surface of the catalyst support and also at least a portion of the impregnated solution from pores of a particular size range in the catalyst support. In this way, the centrifugation step in conjunction with adjustment of the impregnation solution enables control of the silver particle size for each type of pore in the support by tuning the concentration of silver in the pore to match the available surface area within the pore. By selecting the centrifugation speed to provide the proper centrifugal force and centrifugation time, it is possible to control which pore modes remain filled with the silver impregnation solution and therefore control the final silver particle size and the location of the silver particles within the support.

An added benefit of the centrifugation step or steps is that centrifugation can reduce the amount of silver solution left on the exterior surfaces of the support pellet and reduce or even prevent the formation of a silver crust on the pellet surface following calcination. It is hypothesized that the excess silver on the exterior chips off the catalyst during the operation leading to an accumulation of fines and an increase in pressure drop. In addition, removing excess silver solution prior to calcination allows the solution to be recovered and enables better silver utilization in the catalyst production process, reducing production costs.

An additional advantage to producing catalysts in this manner is that it may have overall lower silver loading relative to current state-of-the-art catalyst without a loss of productivity. It will be appreciated that this lower silver loading can reduce the cost of producing such catalyst. In addition, lower silver loading and a reduction of exterior pellet deposition of silver may: (1) cause less pore blockage and therefore reduce diffusional barriers in the catalyst, and (3) reduce subsequent loss of silver during further catalyst handling.

Following the centrifugation step above, the resulting centrifuged support is generally heat-treated, i.e., roasted, at elevated temperatures to evaporate the liquid within the support; and to effect decomposition and reduction of the silver metal salt to metallic silver, thereby effecting deposition of the silver and promoters, if present, onto the interior and exterior support surfaces.

Various heat-treatment atmospheres can be employed for heating the impregnated/centrifuged supports. For example, the support may be heated in air or in an inert atmosphere such as a nitrogen atmosphere. When the heat treatment is done in an oxidative environment, the heat treatment may be referred to as "calcination".

Generally, the silver solution-impregnated support is heat-treated at atmospheric or sub-atmospheric pressure to remove the solvent (or solvents) present and deposit (with or without decomposition) the promoter species, if present, on to the silver and support surfaces. The heat-treatment may be carried out at a temperature and for a period of time sufficient to remove the excess solvent and to convert substantially all of the silver salt to silver metal. For example, the impregnated/centrifuged support can be heated at a temperature of from about 100° C. to about 900° C. in one embodiment, and from about 200° C. to about 700° C. in another embodiment, for a period of time sufficient to convert, i.e. chemically reduce substantially all of the silver salt to silver metal. For example, the roasting step may be carried out for a period of time from about 2 min to about 12 hours (hr). Furthermore, the roasting step may advantageously be carried out under air (in which case the term "calcining" is often used to describe the process), but other gases may also be used, as is generally known in the art.

In general, the higher the temperature, the shorter the period required for chemical reduction. For example, at a temperature of from about 400° C. to about 900° C., chemical reduction of silver species to metallic silver may be accomplished in about 1 min to about 5 min. Other periods of time to thermally treat an impregnated support have been suggested in the art. For example, U.S. Pat. No. 3,563,914 suggests heating an impregnated support for less than 300 seconds to dry, but not to roast to chemically reduce the catalyst; U.S. Pat. No. 3,702,259 discloses heating an impregnated support from 2 hr to 8 hr at a temperature of from 100° C. to 375° C. to chemically reduce the silver salt in the catalyst; and U.S. Pat. No. 3,962,136 suggests 4 hr to 8 hr at a temperature of from 100° C. to 375° C.; all the above patents are incorporated herein by reference. Although a wide range of heating periods can be employed in the present invention, it is preferred that the chemical reduction time be correlated with temperature such that substantially complete chemical reduction of the silver salt to metallic silver is accomplished. A continuous or step-wise heating program is desirably used for this purpose. Continuous roasting of the catalyst for a short period of time, such as for not longer than 4 hr is preferred and can be effectively done in making the catalysts of this invention. When more than one roasting step is used, it is not necessary that the roasting conditions be the same in each roasting step.

The roasting or calcination step of the present invention, and/or any of the other steps thereof, may be a batch or a continuous process. The step of the present invention process including heating the impregnated porous support can be carried out using any conventional heating means. For example, the equipment used for such heat treatment may include a static or flowing atmosphere of the gases to effect chemical reduction.

A highly efficient silver-containing epoxidation catalyst useful for the selective oxidation of ethylene to ethylene oxide results from the preparation process described above. The catalyst comprises at least one catalytic species deposited on a porous support; wherein the at least one catalytic species is silver; and wherein the silver deposited on the support has a controlled average particle size in the finished catalyst.

The active components of the highly efficient catalyst produced by the process of the present invention may include silver as the catalytic species, rhenium as a promoter, optionally, a rhenium co-promoter, and optionally other metals.

After being roasted in the heating zone, the silver impregnated catalyst can be weighed; and based upon the weight gain relative to the material prior to impregnation; the weight of silver (weight % silver) on the support can be calculated, assuming complete removal of solvent and precursor materials.

When the desired catalytic species comprises silver, generally, the wt % silver concentration supported on the support may be dependent upon silver concentration in the impregnation solution, the pore volume of the support, and number of impregnation steps used. Generally, the impregnations will desirably be sufficient to allow the appropriate amount of silver to be provided on the support. For example, the amount of silver supported on the support may be an amount greater than about 5 wt % in one embodiment, greater than about 10 wt % in another embodiment, greater than about 15 wt % in still another embodiment, greater than about 20 wt % in yet another embodiment, greater than about 25 wt % in even still another embodiment, greater than about 27 wt % in even yet another embodiment, and greater than about 30 wt % in even still another embodiment, based on the weight of the catalyst. The amount of silver provided in connection with the supports may usually be less than about 70 wt % in one embodiment, and less than about 50 wt % in another embodiment, based on the weight of the catalyst. See for example, US 2014/0371470 A1 incorporated herein by reference.

In other embodiments, the wt % silver on the support can be for example from about 5 wt % to about 70 wt % in one embodiment, from about 5 wt % to about 50 wt % in another embodiment, from about 15 wt % to about 40 wt % in still another embodiment, and from about 15 wt % to about 35 wt % in yet another embodiment. However, in these embodiments, the resulting wt % silver on the support is in excess of what is desired. The use of a surfactant during the catalyst preparation results in a more optimal wt % silver.

The resulting catalyst prepared by the process of the present invention has silver particles in desired sizes in both small and large pores of the support, sufficient to provide an improved overall catalyst performance. Although silver particle size in the finished catalyst is important, the silver particle size may include a broad range. For example, a suitable silver particle size can range from about 10 angstroms (Å) to about 10,000 Å in diameter. Typically, the silver particle size may range from greater than about 100 Å to less than about 5,000 Å in diameter in one embodiment. It is desirable that the silver and any promoters, if employed, be relatively uniformly dispersed within, throughout, and/or on the alumina support. By the process of this invention, the silver particles have a relatively uniform particle size throughout the support as well, i.e. a relatively narrow particle size distribution.

The particle size of silver metal deposited upon the support is a function of the catalyst preparation procedure employed. Thus, the particular choice of solvent and/or complexing agent, silver salt, heat treatment conditions and catalyst support may affect, to varying degrees, the size of the resulting silver particles.

Catalysts according to the present invention may optionally include one or more promoters or co-promoters. For example, known promoters for silver-based, epoxidation catalysts, in addition to rhenium, may include, but are not limited to, molybdenum, tungsten, sulfur, lithium, sodium, manganese, rubidium, and cesium. Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in U.S. Pat. No. 5,187,140, particularly at columns 11 through 15; U.S. Pat. Nos. 6,511,938; 5,504,053; 5,102,848; 4,916,243; 4,908,343; 5,059,481; 4,761,394, 4,766,105, 4,808,738, 4,820,675; and 4,833,261; all patents which are incorporated herein by reference.

The promoters and/or co-promoters, when used, may vary in concentration for example from about 0 wt % to about 1.0 wt % in one embodiment, from about 0.0005 wt % to about 1.0 wt % in another embodiment, and from about 0.005 wt % to about 0.5 wt % in still another embodiment.

In general, the present invention process can be used for oxidizing an olefin compound to an oxide product. One example of an end use where the catalyst of the present invention is advantageously used can be epoxidizing ethylene to ethylene oxide. The performance of the catalyst in such an epoxidation reaction is typically evaluated on the basis of the catalyst's selectivity, activity, and stability during the epoxidation reaction. "Stability" typically refers to how the selectivity and/or activity changes during the time that a particular batch of catalyst is being used, i.e., as more ethylene oxide is cumulatively produced.

For example, after the silver-based supported catalyst is prepared as described above, the catalyst may be used in a process for epoxidizing ethylene to form an ethylene oxide, as disclosed in US 2014/0323295 A1, incorporated herein by reference. The reaction process of an epoxidation of ethylene is also described, for example, in U.S. Pat. Nos. 6,511,938 and 5,057,481; and Kirk-Othmer, Encyclopedia of Chemical Technology, 4th Ed. (1994) Volume 9, pages 915-959; herein incorporated by reference.

Typically, epoxidation reactions may desirably be carried out in the gas phase, with a feed comprising ethylene and oxygen being caused to come in contact with the epoxidation catalyst of the present invention. Generally, the catalyst is present as a solid material, and more particularly, may be present as a packed bed within a desired reactor. The quantity of catalyst used may be any suitable amount and will depend upon the application. In one embodiment, the conversion of ethylene to ethylene oxide can be carried out, for example, in a continuous process by continuously introducing a feed stream containing ethylene and oxygen or an oxygen-containing gas to a catalyst-containing reactor. The resulting ethylene oxide is separated and recovered from the reaction products using conventional methods.

The reactor used for the conversion of ethylene to ethylene oxide using the catalysts described herein may be of a variety of reactor types, including, fixed bed tubular reactors, continuous stirred tank reactors (CSTR), and fluid bed reactors, a wide variety of which are well known to those skilled in the art and need not be described in detail herein.

Oxygen may be supplied to the reaction in an oxygen-containing stream, such as, air or as commercial oxygen, or as oxygen-enriched air. The concentration of oxygen in the reactor feed stream may vary over a wide range, and in practice, flammability is generally the limiting factor for oxygen concentration. Generally, the oxygen concentration in the reactor feed will be at least one (1) mole percent, preferably at least two (2) mole percent, and still more preferably at least four (4) mole percent. The oxygen concentration will generally be no more than fifteen (15) mole percent, preferably no more than twelve (12) mole percent, and even more preferably no more than nine (9) mole percent.

The concentration of ethylene in the reactor feed stream may vary over a wide range. However, it is preferably at least eighteen (18) mole percent and more preferably at least twenty (20) mole percent. The concentration of ethylene in the reactor feed stream is preferably no greater than 50 mole percent, and more preferably is no greater than 40 mole percent.

Generally, the epoxidation reaction is carried out at a temperature of from about 180° C. to about 315° C., and at a reactor pressure in the range of from about atmospheric to about 35 bar. The gas hourly space velocity (GHSV) may be greater than about 3,000 h$^{-1}$. The residence times in the large-scale catalyst-containing reactors are generally on the order of from about 0.5 seconds to about 2.5 seconds. The above epoxidation process conditions are generally employed depending upon the mass velocity and productivity desired.

Examples

The following examples further illustrate the present invention in more detail but are not to be construed to limit the scope thereof.

Ethylene oxide catalysts are prepared using the "double dip" impregnation process. In this process, porous α-alumina carrier is vacuum-impregnated with the silver-containing solution and subsequently roasted. The comparative examples are designed to mimic current practice in that no surfactants are used. In the inventive examples either 0.1 or 1.0 wt % of surfactants are dissolved into the solution prior to the impregnation step.

Alumina carrier (Norpro A-LAP-C1-5 obtained from the Saint Gobain Corporation; 1.29 m$^2$/g surface area, 0.70 cm$^3$/g pore volume) is used as-received for all catalysts prepared in this study. Carrier pellets are loaded into a vacuum flask, sealed on the top by a Teflon stopper containing a vertical through hole and vacuum sidearm. The glass drain tube of a separation funnel is inserted into the vertical hole and held in place by a compression fitting with a rubber o-ring to ensure a good seal. The alumina carrier is evacuated at 70 torr for 15 minutes by a mechanical pump connected through a trap submerged in ice water. The silver-containing impregnation solution, such as the silver-amine-oxalate solutions prepared as described under "Catalyst Preparation" in U.S. Patent Application Publication No. 2009/177000, containing either 0, 0.1% or 1.0% surfactant is poured into the separation funnel, while the vacuum line to the vacuum flask is closed. The stopcock on the separation funnel is then opened, covering the evacuated alumina carrier pellets with the impregnation solution. Vacuum is then broken to atmosphere and the pellets are allowed to soak for 15 minutes.

After soaking, the bottom stopcock of the vacuum flask is opened, allowing excess silver-containing impregnation solution to drain from the catalyst pellets for 10 minutes. Wet catalyst pellets are then placed in a wire-mesh basket and inserted into a muffle furnace pre-heated to 500° C., where they are roasted for 5 minutes.

The vacuum impregnation procedure is repeated for a second impregnation with the exception that promoter precursors are first dissolved in the silver-containing impregnation solution.

Reduction of Silver Impregnation Solution Picked Up by the Alumina Carrier

In order to ascertain the effectiveness of various surfactants in reducing the usage of silver impregnation solution, dry α-alumina carrier is weighed before its impregnation by surfactant-containing solution and after impregnation and draining. The amount of the silver solution the carrier should theoretically absorb is known from its measured specific pore volume and from the density of the solution. As seen in FIG. 1, in all cases, the amounts of the silver impregnation solution retained are higher than the theoretical amount in all cases. The amount of the solution retained over the theoretical amount by the catalyst carrier when the impregnation solution doesn't contain any surfactant is about 20%, while the amounts of the same solution retained in the presence of surfactant ranges between 2.9 and 9.7%. The difference between the amounts of silver solution retained on the catalyst pellets without and with surfactant represents improved recovery of the excess impregnation solution, allowing it to be potentially reused for subsequent impregnations. As the use of surfactant did not completely eliminate the retention of extra-pore silver solution, further opportunities to improve the process are still possible, for example by combining the use of surfactants with centrifugation or by combining different types of surfactants in varying concentrations.

Figure 2:
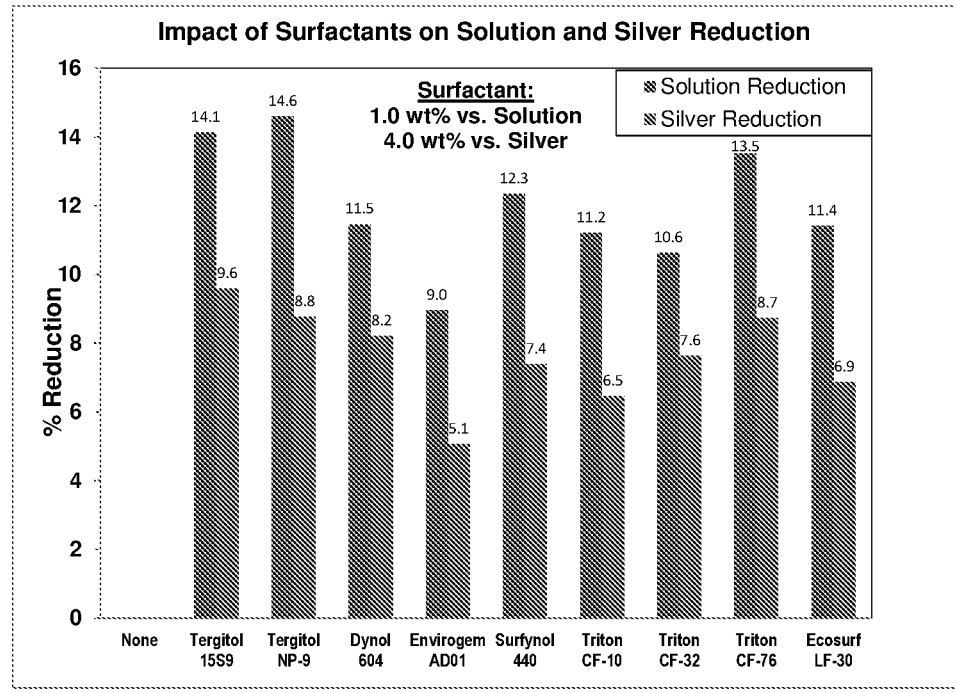
FIG. 2 is a graphical representation showing the effectiveness of various surfactants in reducing the amount of silver impregnation solution and the amount of metallic silver used in the synthesis of EO catalysts.

The improved utilization of silver-containing solution in synthesis of catalysts using various surfactants relative to a catalyst prepared using no surfactants are calculated and plotted in FIG. 2. In this plot, surfactant-modified catalysts with improved utilization of the solution and silver, e.g. both TERGITOL™s and TRITON™ CT-76 (FIG. 1) had the lowest solution uptakes over the carrier pore volume (FIG. 1). The reduction values of silver solution in all catalysts are consistently 1.4-1.8 times larger than the respective silver metal reduction values. We believe that the observed differences between the reductions of silver solution and metallic silver resulted from a loss of excess silver solution in the No Surfactant comparative example during roasting.

Figure 3:
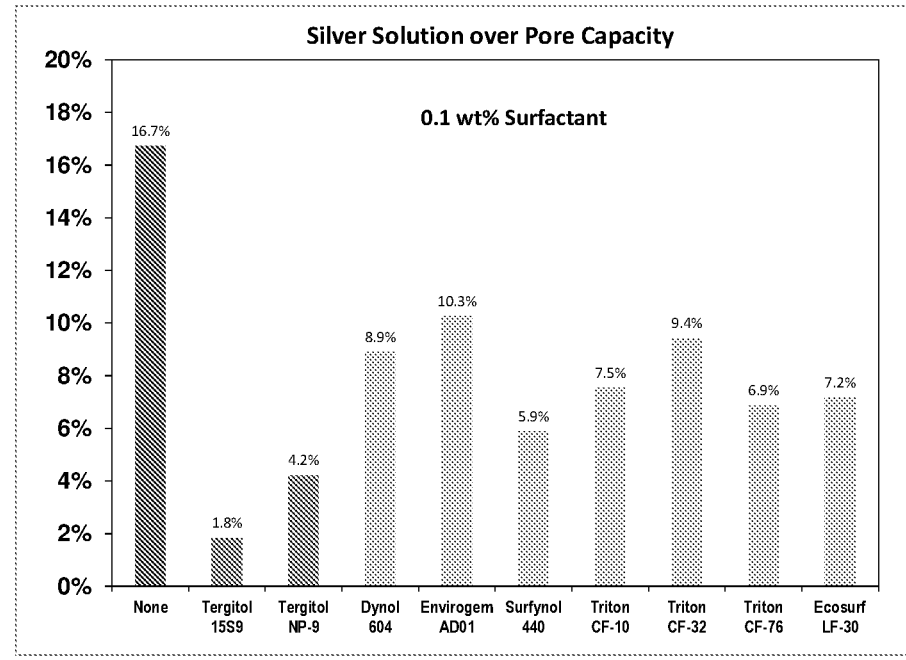
FIG. 3 is a graphical representation showing the effectiveness of various surfactants added at 0.1% by weight, in allowing excess silver impregnation solution to drain from the support.

Next, the alumina carrier was impregnated with silver solutions containing 0.1% of surfactant amounts, and the solution amounts retained on the catalyst support over the theoretical volume were also calculated (FIG. 3).

The amount of the silver solution retained by the carrier over the pore capacity using no surfactant is about 16.5% (FIG. 3) compared with about 20% (FIG. 1) found during the previous set of measurements. The difference likely results from the experimental error associated with weighing moist catalyst that may lose some of the externally retained HEC solution during handling and transfer. However, both values demonstrate that there is a need to improve the utilization of the silver impregnation solution.

Figure 4:
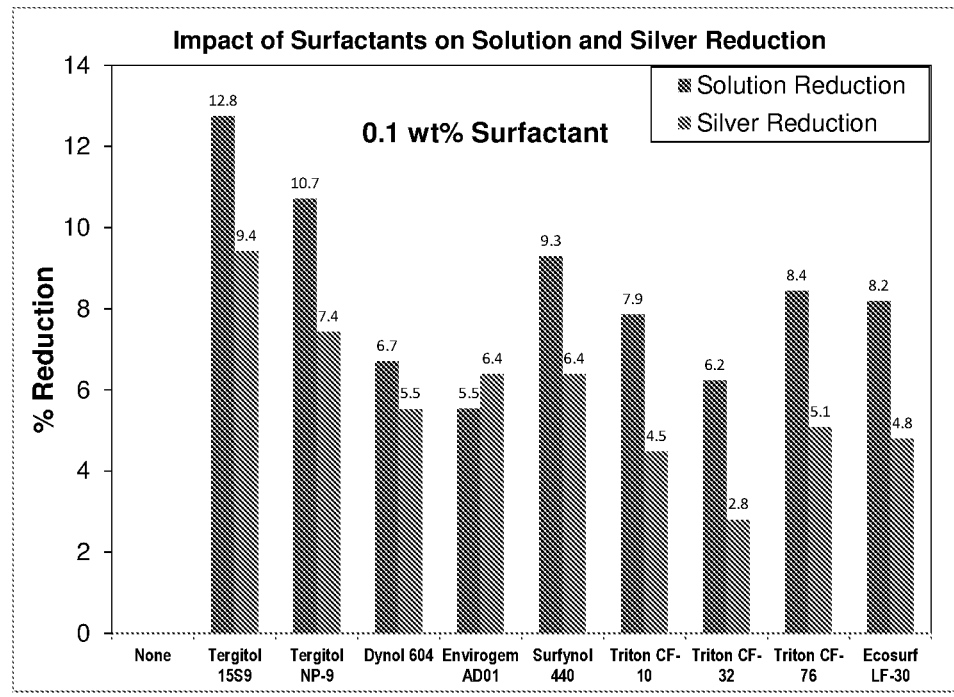
FIG. 4 is a graphical representation showing the effectiveness of various surfactants in reducing the amount of the silver impregnation solution and metallic silver used in the synthesis of EO catalysts.

The reductions of the pickup of silver solution resulting from the use of 0.1% surfactants relative to the solution pickup using no surfactant are shown in FIG. 4. The reductions of silver amounts collected on the catalyst resulting from the use of 0.1% surfactants relative to no surfactant used are shown in the same figure. The values of apparent reduced usage of metallic silver on dry catalyst are smaller than the reduced usage of silver-containing solution, as was observed in the catalyst series prepared with 1% surfactants. Again these rather systematic differences were likely caused by the silver-containing solution lost during the roasting of the catalyst prepared using no surfactant.

Catalytic Performance of EO Catalysts Prepared Using Surfactants

The improved utilization of silver-containing impregnation solution during the preparation of the EO catalyst is desired in order to reduce the catalyst cost and increase roasting throughput. In order for the cost reduction to prove valuable, the performance of EO catalyst should not suffer relative to the catalyst during the synthesis of which no surfactant was used.

The catalytic performance of surfactant-modified catalysts is measured using Rotoberty™ reactors. An equal amount of 45 mL of catalyst is loaded into each Rotoberty reactor. Two output parameters are monitored as a measure of catalyst performance: the rate of production of ethylene oxide in the product stream, and the carbon efficiency in converting ethylene precursor into ethylene oxide. These parameters were calculated in the same way for each example. In high-performing catalyst, both these quantities are maximized.

Figure 5:
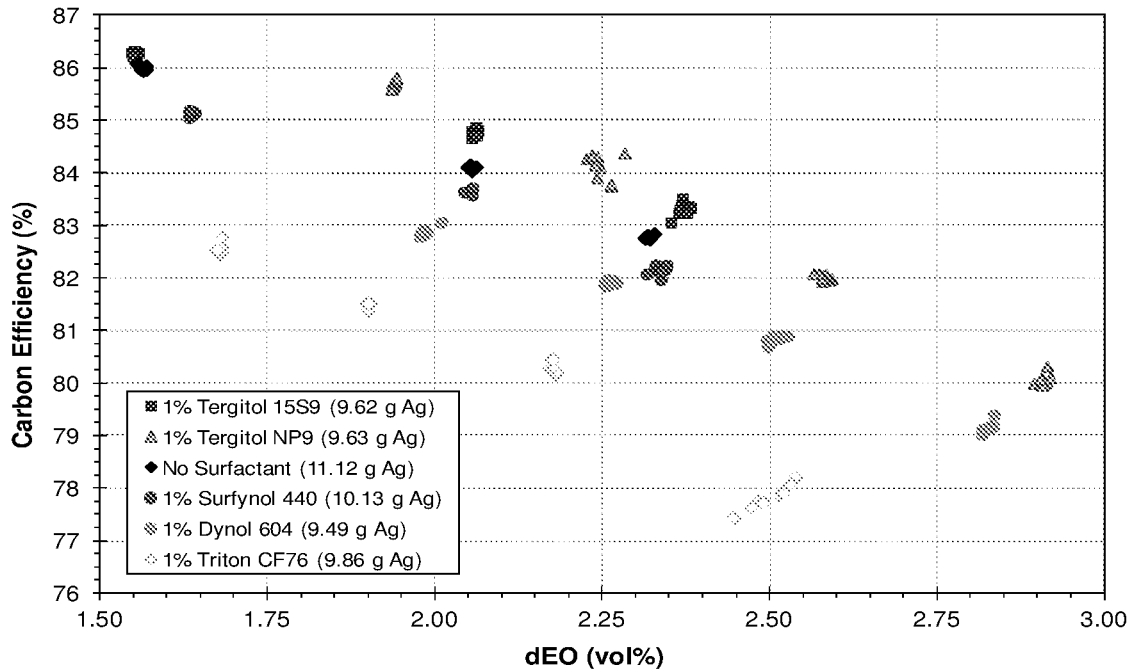
FIG. 5 is a graphical representation of the performance of the catalysts prepared using 1.0 weight percent of various surfactants.

FIG. 5 shows a plot of carbon efficiency of various surfactant-modified catalysts as a function of evolving EO for several catalysts prepared with 1 wt. % surfactants. The catalysts modified with 1% TERGITOL™ 15S9 and 1% TERGITOL™ NP-9 appear to show a slightly higher performance than the catalyst containing no surfactant. The apparent differences between these three catalysts are relatively small and the relative performance values are probably within the margins of measurement errors. The similar performance characteristics in these catalysts, however, are achieved with different amounts of silver: The EO catalyst prepared without any surfactants contained about 11.1 g of silver, while both TERGITOL™-modified catalysts contained only about 9.6 g, i.e. roughly 13% less silver.

The performance of other surfactant-modified catalysts appear to decrease in the order Surfynol®>DYNOL™>TRITON™ CF76. The performance of the former two catalysts is probably within the margin of error of the comparative example with no surfactant in the catalyst solution. As in the case of both TERGITOL™-modified catalysts, the amounts of silver contained in the latter catalysts is lower than the silver content in the comparative example without any surfactant.

Figure 6:
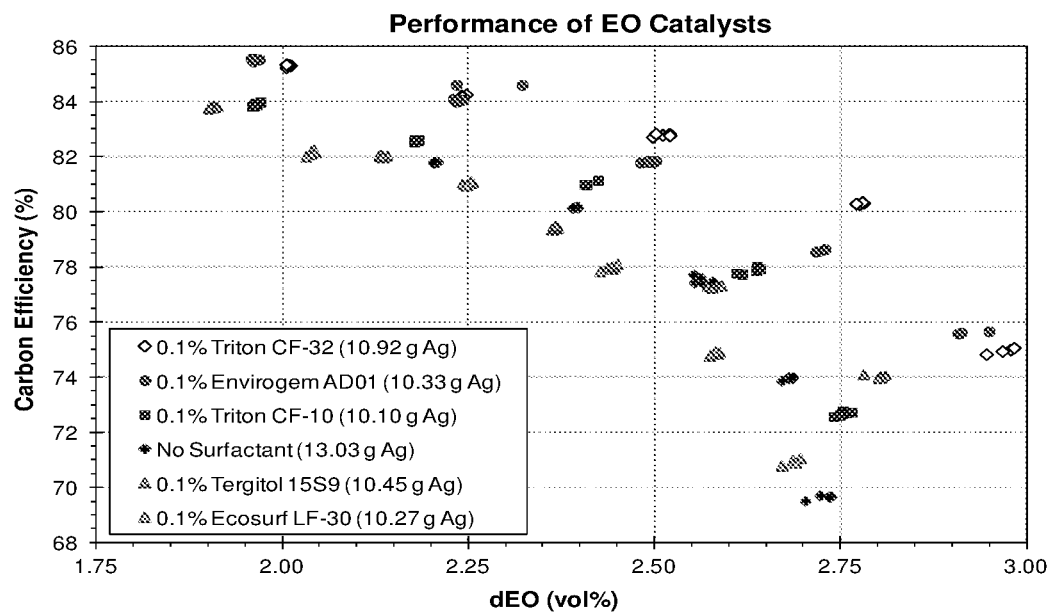
FIG. 6 is a graphical representation of the performance of the catalysts prepared using 0.1 weight percent of various surfactants.

Performance characteristics of EO catalysts prepared using of 0.1% surfactants were also determined (FIG. 6). In these catalysts, the relative performance seems to decrease in the following order: TRITON™ CF32>ENVIROGEM® ADO1>TRITON™ CF-10>No Surfactant>TERGITOL™ 15S9>ECOSURF™ LF-30. The differences between the catalysts adjacent to each other in performance are quite small, but the difference between the catalysts at the opposite ends of the performance spectrum is not negligible.

These results suggest that catalysts with less silver can give equivalent or improved performance relative to the catalyst prepared using standard methodologies. Additional testing is necessary to demonstrate that the use of less silver does not result in poorer performance with increased time on stream.

What is claimed is:

1. A process for preparing a silver-containing catalyst suitable for the oxidation of ethylene to ethylene oxide (EO) comprising the steps of:
   (a) providing a support having pores;
   (b) providing a silver-containing impregnation solution;
   (c) adding an amount of surfactant to the impregnation solution to form a surfactant-containing impregnation solution, wherein the surfactant is added to the impregnation solution in an amount of from 0.4% by weight to 4.0% by weight of silver in the impregnation solution;
   (d) contacting the support with the surfactant-containing impregnation solution after step (c);
   (e) removing at least a portion of the surfactant-containing impregnation solution prior to fixing the silver upon the carrier in a manner which preferentially removes the surfactant-containing impregnation solution not contained in the pores.

2. The process of claim 1 further comprising the additional step of:
   (f) roasting at least once, the impregnated catalyst support member from step (d).

3. The process of claim 1, wherein the preferential removing step (d) is carried out using a centrifuge.

4. The process of claim 1, wherein the removing step (e) is carried out by allowing the impregnated catalyst support member to drain using gravity.

5. The process of claim 1, wherein the impregnation step d) is carried out two or more times; or wherein the removing step (e) is carried out two or more times and under two or more different process conditions.

6. The process of claim 1 wherein the support has a first set of support pores having a first size range and at least a second set of support pores having a second size range wherein the second size range is smaller than the first size range, and wherein the removing step (d) preferentially removes surfactant-containing impregnation solution contained in the first set of support pores of the porous multimodal catalyst support as compared to surfactant-containing impregnation solution contained in the at least second set of pores of the porous multimodal catalyst support.

7. The process of claim 6, wherein the first pore size range of the first set of pores of the support is from 3 microns to 200 microns; and wherein the second pore size range of the second set of pores of the support is from 0.01 micron to 3 microns.

8. The process of claim 1 wherein the surfactant is one or more of nonylphenol ethoxylates, alkyl polyglucosides, phosphate esters, secondary alcohol alkoxylates, alkylphenyloxide disulfonate salts, low foam surfactants, sulfates or sulfonates.

9. The process of claim 1, wherein the impregnation solution further comprises one or more promoters.

10. The process of claim 1, wherein the support comprises alpha-alumina.

11. The process of claim 1, wherein a silver loading of at least 10 weight percent is provided on the porous support, based on the total weight of the porous support.

12. A process for the epoxidation of ethylene to ethylene oxide, comprising contacting ethylene and oxygen in the presence of an epoxidation catalyst produced according to the process of claim 1.

13. The process of claim 1, wherein the surfactant is added to the impregnation solution in an amount of from 0.05% by weight of the impregnation solution.

\* \* \* \* \*